United States Patent [19]

Fowles et al.

[11] Patent Number: 5,423,753
[45] Date of Patent: Jun. 13, 1995

[54] VIAL ADAPTER

[75] Inventors: Thomas A. Fowles, McHenry; Nick Fotis, Crystal Lake; Charles Eller, Antioch, all of Ill.; Brian J. Gorman, Lake Geneva, Wis.; Mark A. Hoekwater, Vernon Hills, Ill.

[73] Assignee: Baxter International Inc., Deerfield, Ill.

[21] Appl. No.: 260,616

[22] Filed: Jun. 16, 1994

Related U.S. Application Data

[63] Continuation of Ser. No. 86,436, Jun. 19, 1993, abandoned.

[51] Int. Cl.6 .......................................... A61M 37/00
[52] U.S. Cl. ........................................ 604/87; 604/85; 604/413
[58] Field of Search ............... 604/411, 412, 413, 414, 604/82, 83, 85, 88, 87

[56] References Cited

U.S. PATENT DOCUMENTS

| | | | |
|---|---|---|---|
| 4,020,839 | 5/1977 | Klapp | 604/414 |
| 4,588,403 | 5/1986 | Weiss et al. | 604/414 |
| 4,759,756 | 7/1988 | Forman et al. | 604/413 |
| 4,804,366 | 2/1989 | Zbeb et al. | 604/85 |
| 4,850,978 | 7/1989 | Dudar et al. | 604/201 |
| 5,049,129 | 9/1991 | Zbeb et al. | 604/413 |
| 5,061,264 | 10/1991 | Scarrow | 604/414 |
| 5,074,844 | 12/1991 | Zdeb et al. | 604/85 |
| 5,167,642 | 12/1992 | Fowles | 604/263 |

FOREIGN PATENT DOCUMENTS 3229783  1/1984  Germany .................... 604/413

Primary Examiner—John G. Weiss
Attorney, Agent, or Firm—Mark J. Buonaiuto; Amy L. H. Rockwell; Paul C. Flattery

[57] ABSTRACT

An adapter for interconnecting in fluid communication a first connection site and a beneficial agent container having a closure. The adapter includes a plate having first and second connection site sides. A wall extends from the plate from the second connection site side and constructed to surround only the closure. This allows containers having varying sized bodies to be received. A cannula structure is rigidly secured in the plate and defines a flow path extending through the plate. The adapter can be provided in an assembly with the beneficial agent contained or in a drug delivery system.

14 Claims, 4 Drawing Sheets

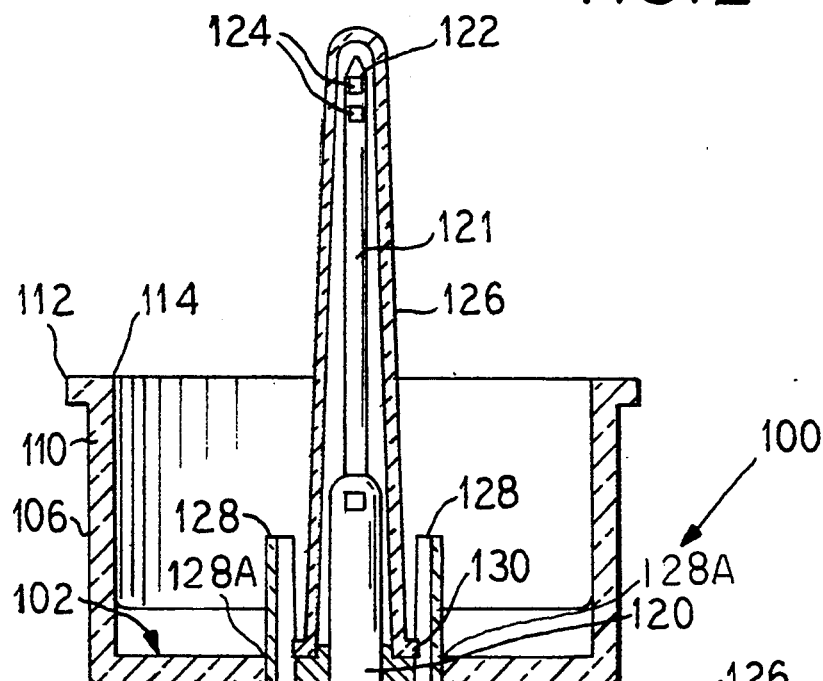
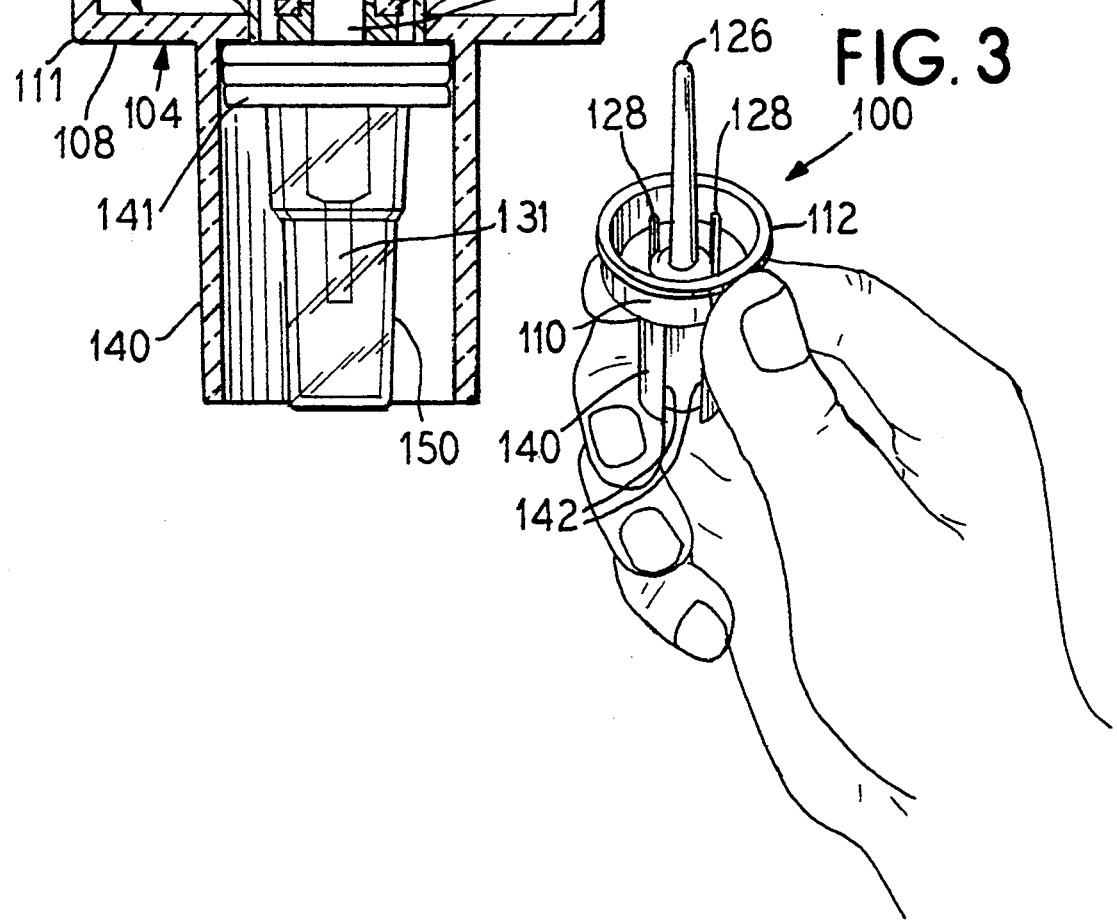
FIG. 2
FIG. 3

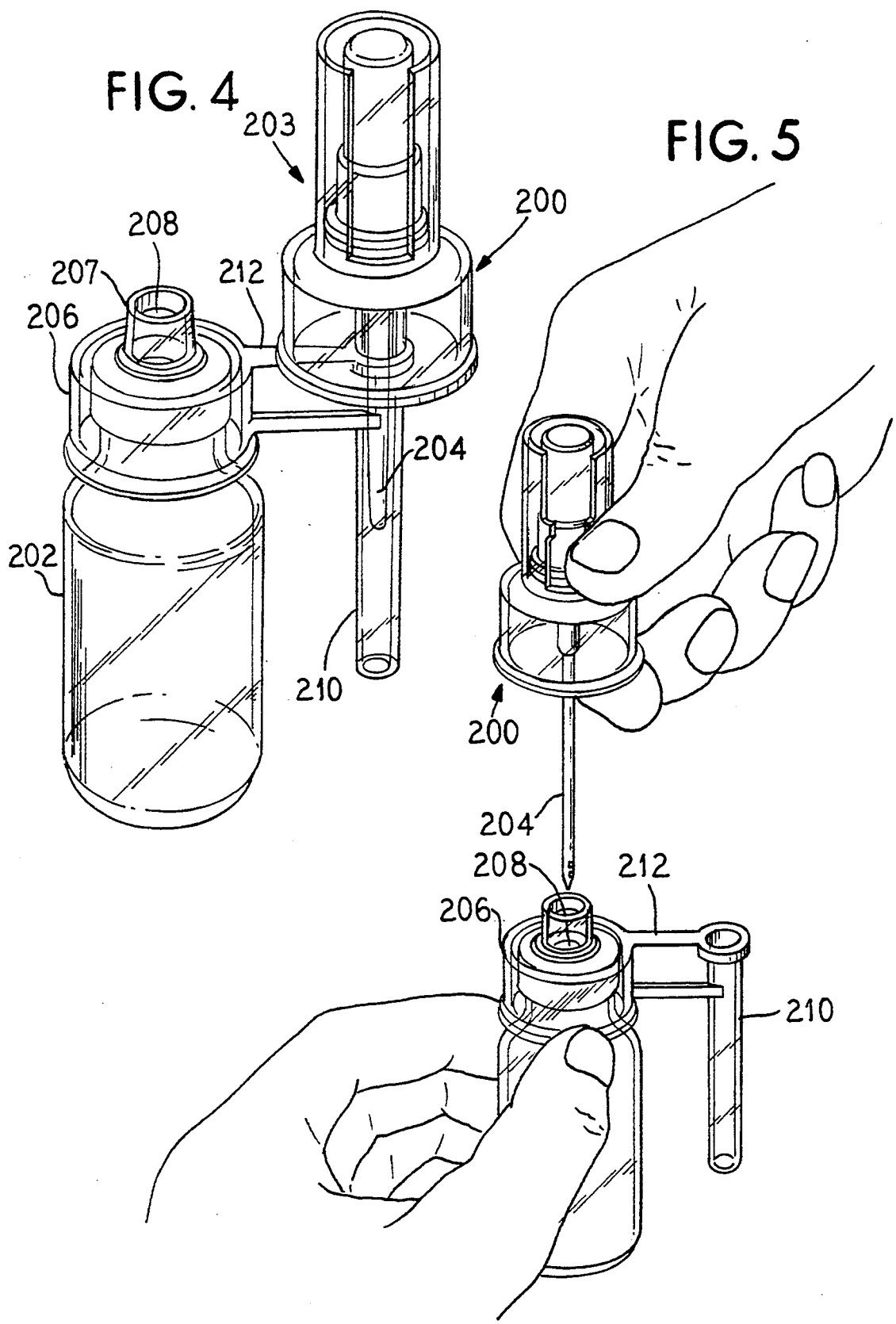

VIAL ADAPTER

This is a continuation of application Ser. No. 08/086,436, filed on Jun. 30, 1993, now abandoned.

BACKGROUND OF THE INVENTION

The present invention generally relates to delivery systems for delivering a beneficial agent to a patient. More specifically, the invention relates to means for attaching vials to connection sites.

Many drugs are mixed with a diluent before being delivered intravenously to a patient. The diluent may be, for example, a dextrose solution, a saline solution or even water. Many such drugs are supplied in powder form and packaged in glass vials or ampules. Other drugs, such as some used in chemotherapy, are packaged in glass vials or ampules in a liquid state.

Powdered drugs may be reconstituted in a well known manner, utilizing a syringe which is used to inject liquid into the vial for mixing, the syringe eventually withdrawing the mixed solution from the vial. When a drug must be diluted before delivery to a patient the drug is often injected into a container of diluent after it is reconstituted, where the container may be connected to an administration set for delivery to a patient. More specifically, the diluent is often packaged in glass bottles, or flexible plastic containers such as are sold under the names MINI-BAG TM and VIA-FLEX ® by Baxter Healthcare Corporation of Deerfield, Ill. These containers have administration ports for connection to an administration set which delivers the container contents from the container to the patient. The drug is typically added to the container through an injection site on the container.

Drugs may be packaged separately from the diluent for various reasons. One of the most important reasons is that many drugs do not retain their chemical and physical stability when mixed with a diluent and thus cannot be stored for any substantial period of time. Also, drugs are often packaged separately from the diluent because many firms which manufacture drugs are not engaged in the business of providing medical fluids in containers for intravenous delivery, and vice versa.

Therefore, a doctor, nurse, pharmacist or other medical personnel must mix the drug and diluent. This presents a number of problems. The reconstitution procedure is time consuming and requires an aseptic technique. The operator must provide the proper diluent and a syringe before beginning. Often the powdered drug is "caked" at the bottom of the vial. Thus, when liquid is injected into the vial from a syringe the surface area of contact between the liquid and the powdered drug may be quite small initially, thus making the mixing procedure even more time consuming.

Because of the limited vial volume, the increasing drug concentration in the diluent makes it harder to finish the reconstitution process. The operator may attempt to solve this by repeatedly injecting solution into the vial, mixing and withdrawing the solution. This technique requires additional injections and movement of the syringe which increase the likelihood of contamination. Also, it is sometimes difficult to get all of the drug and/or liquid out of the vial, thus increasing the time required to perform the reconstitution procedure.

The reconstitution procedure should be performed under preferably sterile conditions. In addition to such a requirement making the operator justifiably more cautious and consuming more time, sterile conditions are often hard to maintain. In some instances, a laminar flow hood may be required under which the reconstitution procedure is performed.

Some drugs, such as some chemotherapy drugs, are toxic. Exposure of the operator to the drugs during reconstitution may be dangerous, especially if the operator works with such drugs on a daily basis and is repeatedly exposed to them.

A further problem is that the reconstitution procedure provides a source of confusion as to which container contains which drug. The diluent container should be marked with the drug with which it has been injected and the name of the patient to whom it should be delivered.

After a drug is reconstituted and withdrawn into a syringe barrel, the drug may in some instances be injected immediately into the intravenous system of a patient. More typically, however, the reconstituted drug is injected from the syringe into a larger container of solution as discussed above, for connection to an intravenous administration set. This is because often the drug reconstituted in the syringe is still at a concentration so high as to cause local toxicity in the veins of a patient near the injection site where the needle pierces the skin. This may create severe vein irritation which may be medically harmful.

Additionally, even though the proper dose of medication is in the syringe, immediate injection into the patient's blood stream may create a condition of systemic toxicity wherein the level of drug concentration in the patient's entire blood stream is dangerously high. Yet another reason for not making the injection from the syringe directly into the patient is that it creates an additional injection site into the patient, which may be painful for the patient and provides another opportunity for infection.

For these reasons, the reconstituted drug is more typically injected into a diluent container.

A patient may typically be administered a dextrose or saline solution from a large volume parenteral container, for example, such as a one liter container, delivered through an administration set such as a CONTINUFLO ® administration set sold by Baxter Healthcare Corporation. If the reconstituted drug were injected into the large volume parenteral container, delivery of the drug would usually be made over too long a time period. Often, these large volume fluids are delivered at very slow flow rates.

More typically, the reconstituted drug is injected into a small volume parenteral container, such as a fifty milliliter container sold by Baxter Healthcare Corporation. This MINIBAG TM container is hung at a higher elevation than the large volume parenteral container and is connected by a secondary administration set to an injection site on the primary administration set. Because it is maintained at a higher elevation, the reconstituted drug in the small volume container is delivered, after which fluid from the large volume container begins to flow once more. By utilizing a small volume container connected to an administration set for delivery of the drug or other beneficial agent instead of a direct syringe injection, the drug is delivered over a preferred time period that tends to minimize negative side effects.

U.S. Pat. No. 5,049,129 discloses a passive drug reconstitution and delivery system with liquid flowing through an administration set. A receptacle mounted in the administration set is adapted for receiving a cartridge containing a beneficial agent. Also disclosed are adapter means for connecting the cartridge or a vial and the receptacle and an air flask within the administration set. One adapter includes an enlarged vial end constructed to snap fit about the mouth of a standard vial and a hollow shell configured to engage the receptacle. A sliding plate is positioned within the hollow shell and includes two separate cannulas acting as flow path means, for creating fluid paths through the vial to ensure proper mixing of the beneficial agent within the vial.

U.S. Pat. Nos. 4,804,366 and 4,850,978 disclose drug delivery systems with other adapters designed for use in the cartridges of those systems in which the cannula structures are rigidly mounted. However, in the disclosed adapters, the outside diameter of the vials useable therein is limited as a function of the interior diameter of the adapter.

SUMMARY OF THE INVENTION

The present invention provides an adapter for interconnecting a vial containing a beneficial agent and a drug delivery system. The adapter is constructed such that a variety of vial sizes can be used.

In an embodiment, the invention provides an adapter for interconnecting in fluid communication a first connection site and a chamber for containing a beneficial agent. The adapter includes a plate having first and second connection site sides, a wall extending from the plate from the second connection site side and constructed to engage only the second connection site, and a cannula structure rigidly secured in and extending through the plate.

In an embodiment of the invention, the adapter further comprises a pair of detachable covers secured on opposite sides of the plate and about the cannula to maintain same in an initial sterile condition.

In an embodiment of the invention, the adapter further comprises a tubular keyway member extending coaxially about the cannula from the first connection site side of the plate.

In an embodiment of the invention, the adapter further comprises a pair of detachable covers secured on opposite sides of the plate and about the cannula to maintain same in initial sterile condition. A tubular keyway member extending coaxially about the cannula from the first connection site side of the plate, the tubular keyway member positioned coaxially about the cover secured about the cannula on the first connection site side.

In an embodiment of the invention, the wall extending from the plate includes a radially outwardly extending lip.

In an embodiment of the invention, the adapter further comprises a pair of pins extending from the second connection site side and a cover secured about an end of the cannula extending from the second connection site side and to the pins.

In an embodiment, the invention provides a beneficial agent container and adapter assembly, comprising a beneficial agent container having a chamber within which can be contained a beneficial agent and a closure end having a pharmaceutical connection site. An adapter is provided that is configured to interconnect in fluid communication with the beneficial agent container and a second connection site, the adapter including a plate having first and second connection site sides, a tubular wall extending from the first connection site side and constructed such that the tubular wall engages only about the first pharmaceutical connection site of the beneficial agent container. A support is secured to the beneficial agent container and to the adapter for supporting same in an initial assembly, the adapter being detachably attached to the support.

In an embodiment, the invention provides a beneficial agent delivery system comprising a receptacle configured to deliver fluid to a patient, including a connection site by means of which a beneficial agent can be introduced into the delivery system. An adapter is provided for interconnecting in fluid communication the connection site of the delivery system and a beneficial agent container with a second connection site and a chamber for containing a beneficial agent, the adapter including a plate having first and second connection site sides, a wall extending from the plate from the second connection site side and configured to engage only the second connection site of the beneficial agent container, and a cannula structure rigidly secured in the plate and having a cannula extending through the plate. And a beneficial agent container is provided having the second connection site.

Additional features and advantages of the present invention are described in, and will be apparent from, the detailed description of the presently preferred embodiments and from the drawings.

BRIEF DESCRIPTION OF THE DRAWINGS

FIG. 2 illustrates in fragmentary cross-sectional view an adapter embodying principles of the invention.

FIG. 3 illustrates in perspective view the adapter of FIG. 2 being held by a user.

FIG. 4 illustrates an adapter secured in a holder connected to a vial.

FIG. 5 illustrates insertion of a cannula of the adapter of FIG. 4 into the vial of FIG. 4 by a user.

DETAILED DESCRIPTION OF THE PRESENTLY PREFERRED EMBODIMENTS

As described above, the present invention provides an adapter that will connect a variety of vial sizes to an injection site. To that end, the adapter includes a side of which is (vial side) configured to be connected to variously sized vials and a connection site side configured to be connected to a connection site.

Figure 1:
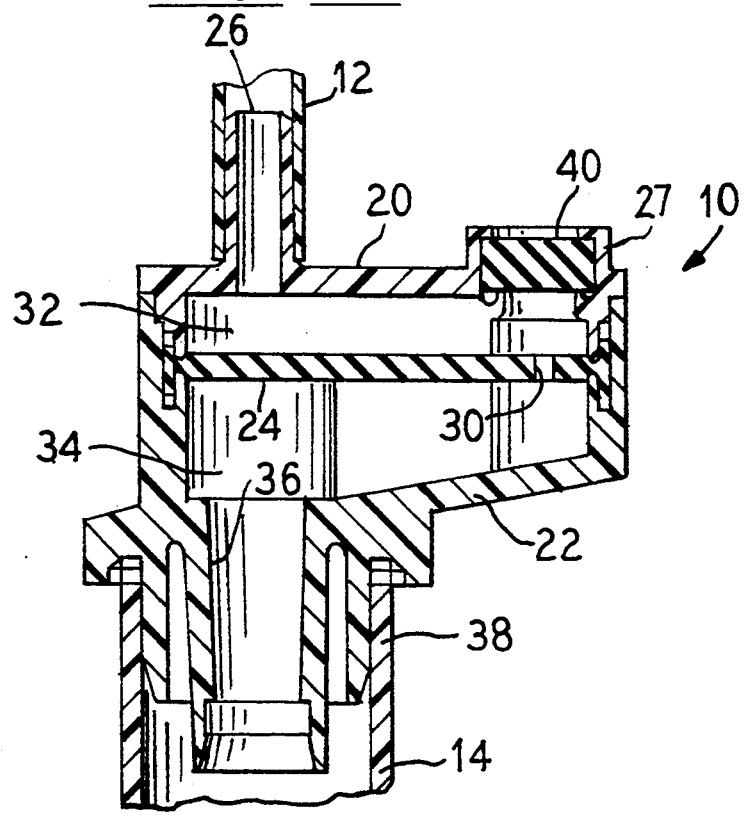
FIG. 1 illustrates a receptacle including an injection site and an administration set.

In FIG. 1, there is illustrated a receptacle 10 such as that illustrated and described in U.S. Pat. Nos. 4,804,366 and 4,850,978, the disclosures of which are fully incorporated herein by reference. The receptacle 10 forms part of an administration set and is interconnected between a fluid delivery conduit 12 and an air flask 14.

As disclosed in U.S. Pat. Nos. 4,804,366 and 4,850,978, the receptacle 10 is configured to accept fluid flow from the conduit 12 and to redirect the fluid through a beneficial agent containing container, such as a vial, so that a drug in the chamber can be reconstituted and then delivered to a patient through the remainder of the administration set following downstream of the air flask.

Briefly, the receptacle 10 is constructed such that it is provided with upper and lower fitments 20 and 22 having secured therebetween a divider 24. The upper fitment 20 includes an inlet 26 to which is attached the fluid conduit 12 and a connection site 27 within which is secured a rubber or rubber-like injection site 40. The divider 24 includes a through bore 30 which normally would allow a fluid to flow from an upper chamber 32 defined by the divider 24 and the upper fitment 20 and a lower chamber 34 defined by the lower fitment 22 and the divider 24. The lower fitment 22 contains an outlet 36 connected to an inlet 38 of the air flask 14.

As is illustrated and as is described in greater detail in U.S. Pat. Nos. 4,804,366 and 4,850,978, the connection of a cartridge to the receptacle 10 to the connection site 27 causes a cannula of the cartridge to extend through the through bore 30. This will block the through bore 30 such that fluid must flow upwardly through a flow path provided in the cartridge and the injection site 40, through the beneficial agent up to an upper end of the cannula and thence downwardly through the cannula and out through the chamber 34 to the outlet 36.

As is also described in U.S. Pat. Nos. 4,804,366 and 4,850,978, the beneficial agent containing chamber can be provided in the cartridge or can be connected to a separate adapter that itself is then connected to the injection site 40. It is this type of adapter that is the subject of this invention.

In this regard, illustrated in FIGS. 2 and 3 is an embodiment of an adapter of the present invention. In FIGS. 2 and 3, there is illustrated an adapter 100 configured for connecting a vial to a connection site. As will be appreciated, the adapter 100 has a vial side 102 configured to be connected to a vial and a connection site side 104 configured to be connected to a connection site, for example, the connection site 27 of the receptacle 10.

As also illustrated, on its vial side 102, the adapter 100 includes a substantially caplike structure 106 having a floor or plate 108 and an upwardly extending tubular wall 110 extending from a periphery 111 of the floor or plate 108. In the illustrated embodiment, the floor or plate 108 preferably is circular, and the wall 110 is annular in shape. An outwardly or radially extending shoulder or lip 112 extends from the wall 110 at a distal end 114 not connected to the periphery 111 of the floor or plate 108.

As can be appreciated, the wall 110 serves as a cover when a vial is connected to the adapter 100. Moreover, the wall 110 is selected to be of a length and constructed such that it engages only the closure of a vial, i.e., that part with a connection site, but not the main enclosure wall of the vial, i.e., that part containing the drug to be reconstituted. Because the wall 110 does not encompass or surround the main portion of the vial, that main portion can be of any size. Thus, various vial sizes can be accommodated on the adapter 100 so long as that portion encompassed by the wall 110 does not exceed the space within the wall 110. For example, the wall 110 can engage any vial including a 20 mm vial closure.

The adapter 100 also includes a cannula structure 120 which is rigidly secured in the plate 108 and which extends concentrically therethrough. The portion of the cannula structure 120 that extends from the vial side 102 forms a needle 121 which is employed to penetrate through the self-sealing anti-contaminant membrane provided over the access opening of a vial. As illustrated, the needle 121 preferably is of the non-coring type, i.e., it has a blunt closed tip 122 with slots 124 which provide fluid communication to a channel interior to the needle 121. Of course, other needle types can be employed if desired.

The adapter 100 preferably includes a sheath 126 for isolating and protecting the needle 121 from contamination prior to use. Although any sheath or cover can be used, in a preferred embodiment, a sheath, such as that disclosed in U.S. Pat. No. 5,167,642, the disclosure of which is hereby incorporated by reference, is used.

Surrounding the sheath 126, in the illustrated embodiment, are a pair of pins 128. The pins 128 extend from the gasket 141 to engage cooperating holes 128A formed in the circular plate 108.

As illustrated, the sheath 126 has a shoulder 130 that extends radially from the sheath 126 and that fits snugly but not too tightly between the pins 128. Openings 128A extend through the plate 108 and receive the pins 128, preferably in an interference fit so that the sheath 126 will not inadvertently become detached from the plate 108.

The portion of the cannula structure 120 that extends from the connection site side 104 is a cannula 131 that is used to penetrate the self-sealing anti-contaminant membrane of an injection site, such as that of the injection site 40. The cannula 131 projects from the center of the plate 108 and serves to provide an outlet from the vial to which the adapter 100 is attached to an injection site.

The cannula structure 120 also includes a shell 140 formed about the cannula 131 so as to provide a fluid path between an outer wall of the cannula 131 and an inner wall of the shell 140. This fluid flow path allows diluent to flow from a source container and into the beneficial agent container where it mixes and dilutes the beneficial agent. Thence, the diluted agent flows through the cannula 131 to the patient. A similar process is described in U.S. Pat. Nos. 4,804,366 and 4,850,978.

On the connection site side 104, the adapter 100 preferably includes a keyway member 140 extending from the base plate 108 and substantially coaxial with the cannula 131. The keyway member 140 may include a relatively rigid tubular keyway wall having a keyway slot 142 for fitting over the connection site. The keyway slot 142 ensures proper engagement of the adapter 100 with the associated receptacle including the proper disposition of the cannula outlet, shell and channel inlet within the receptacle.

The adapter 100 also includes a removable cannula cover 150 removably secured within the base plate 108 and within the keyway member 140. The removable cannula cover 150 has as its principle purpose preventing the connection of the adapter 100 to an injection site without first connecting the adapter 100 to a vial.

In operation, before a beneficial agent in the vial is delivered to the patient, the administration set, of which receptacle 10 is a part, is assembled. This procedure is described more fully in U.S. Pat. No. 4,804,366. The adapter 100 is then connected to a vial substantially as illustrated in FIG. 4, of U.S. Pat. No. 4,804,366, and thence to the receptacle 10.

In FIGS. 4 and 5, there is illustrated an embodiment of the invention wherein an adapter 200 is secured to a vial 202 prior to use in an assembly 203 such that a needle 204 thereof is maintained in a sterile condition. As illustrated, attached to the vial 202 is a cap 206 having a self-sealing anti-contaminant membrane 208 therein and attached to the cap 206 is a needle holder 210. The adapter 200 described above is secured to the needle holder 210 such that the adapter 200 is positioned on an arm 212 extending from the cap 206 attached to the vial 202. Thus, in FIG. 4 the vial and adapter assembly 203 is illustrated in its pre-use state.

When the adapter 200 is to be used, the needle holder 210 is detached from the adapter 200 by appropriate manipulation of the adapter 200, for example, by slight bending back and forth, until the adapter 200 is removed and the needle 204 is removed from the holder 210. The adapter 200 with protruding needle 204 is then connected to the vial 202 as illustrated in FIG. 4.

To this end, the needle 204 is positioned over the membrane 208. The needle 204 is then inserted therethrough and secured to cap 206. The cap 206 in this regard includes an extending member 207 to provide a more stable coupling.

Figure 6:
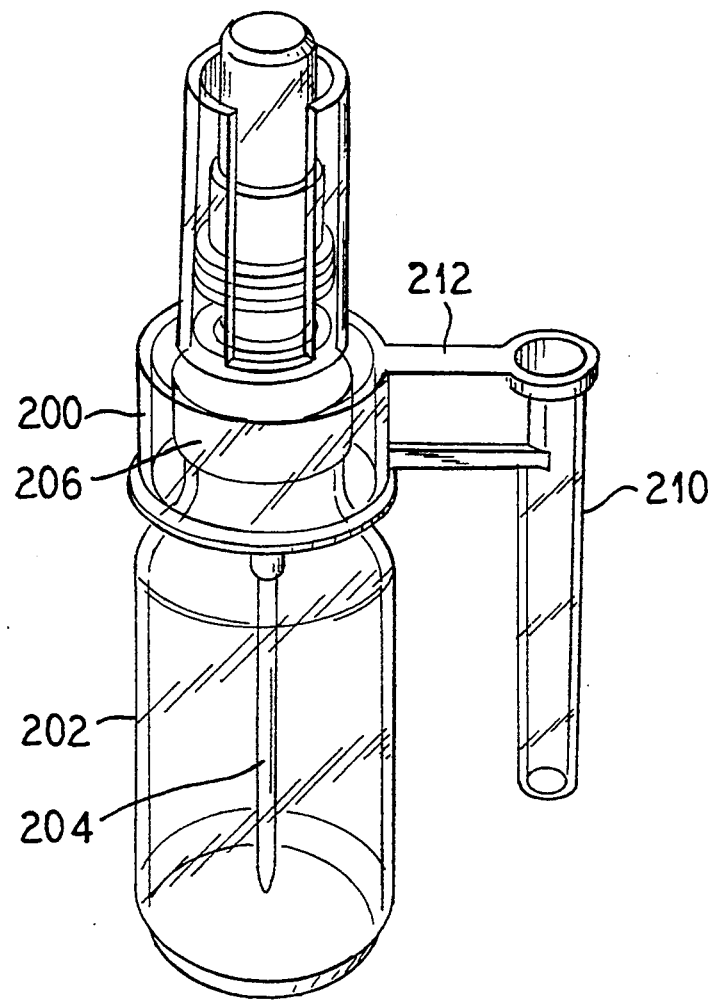
FIG. 6 illustrates an interconnected vial and adapter.

Then, as illustrated in FIG. 6, the adapter 200 is secured about the cap 206 such that the contents of the vial 202 are placed in fluid communication with the needle 204. Thereafter, the vial 202 can be inverted and the adapter 200 can be secured to an injection site such as the injection site 40 of the receptacle 10 to the administration set described above and in the manner described above.

Due to the structure of the cap 206, one is insured that a tight fit is always achieved with the adapter 200. Further, because the cap 206 only engages the closure of the vial, various sized vials can be accessed.

It can further be appreciated that the cap 206 can be structured such that it can be secured to a variety of vials with differently sized closures. However, because the connection site on the cap 206 is of a known standard size, then the adapter 200 need not be altered for different vials. Instead, the adapter 200 can be of a known standard size to cooperate with the known size of the connection site on the cap 206.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. An adapter for interconnecting in fluid communication a first connection site and a beneficial agent container having a body and closure comprising:
    a plate having first and second connection site sides;
    a wall extending from the plate from the second connection site side and constructed to engage about only the closure allowing containers having varying sized bodies to be secured therein;
    a single, removably covered cannula structure rigidly secured in the plate and defining a flow path extending through the plate; and
    a pair of pins extending between the second connection site side and the first connection site side.

2. The adapter of claim 1 further comprising:
    a removable cover secured about a portion of the cannula to maintain same in initial sterile condition; and
    a tubular single keyway member extending coaxially about the cannula from the first connection site side of the plate, the tubular keyway member positioned coaxially about the cover.

3. The adapter of claim 1 wherein the wall extending from the plate includes a radially outwardly extending lip.

4. A beneficial agent container and adapter assembly, comprising:
    a beneficial agent container having a chamber within which can be contained a beneficial agent and a closure having an injection site; and
    an adapter configured to interconnect in fluid communication the beneficial agent container and a second connection site, the adapter including a plate having first and second connection site sides, a tubular wall extending from the first connection site side and constructed such that the tubular wall allows containers having varying sized chambers to be secured thereto, a single removable covered cannula structure rigidly secured in the plate and flow path through the plate;
    a support secured to the beneficial agent container for removably receiving the adapter; and
    a pair of pin extending between the second connection site side and the first connection site side.

5. The beneficial agent container and adapter assembly of claim 4 further comprising:
    a single tubular keyway member extending coaxially about the cannula from the first connection site side of the plate.

6. The assembly of claim 5 further comprising:
    a pair of detachable covers secured on opposite sides of the plate and about the cannula to maintain same in initial sterile condition, the support interconnecting the cover secured to the second connection site side of the plate and the beneficial agent container; and
    a tubular single keyway member extending coaxially about the cannula from the first connection site side of the plate, the tubular keyway member positioned coaxially about the cover secured about the cannula on the first connection site side.

7. The assembly of claim 4 wherein the wall extending from the plate includes a radially outwardly extending lip.

8. The assembly of claim 4 wherein the support includes a cannula receiving member.

9. A beneficial agent delivery system comprising:
    a receptacle configured to deliver fluid to a patient, including a first connection site by means of which a beneficial agent can be introduced;
    an adapter for interconnecting in fluid communication the first connection site of the delivery system and a beneficial agent container having a closure with a second connection site and a chamber for containing a beneficial agent, the adapter including a plate having first and second connection site sides, a wall extending from the plate from the second connection site side and configured to engage about only the closure of the beneficial agent container, and a single removably covered cannula structure rigidly secured in the plate and having a cannula extending through the plate;
    a beneficial agent container having the closure with the second connection site and a chamber within which can be contained a beneficial agent; and
    a pair of pins extending between the second connection site side and the first connection site side.

10. The system of claim 9 wherein the wall extending from the plate includes a radially outwardly extending lip.

11. The system of claim 9 including means for removably coupling the adapter to the beneficial agent container prior to inserting the cannula through the closure.

12. An adapter for interconnecting in fluid communication a first connection site and a beneficial agent container having a body and a closure comprising:
- a plate having first and second connection site sides;
- a wall including a radially outward extending lip which extends from the plate from the second connection site side and constructed to engage about only the closure allowing containers having varying sized bodies to be secured therein;
- a single removably covered cannula structure rigidly secured in the plate and defining a flow path extending through the plate;
- a pair of removable covers secured on opposite sides of the plate and about the cannula to maintain same in an initial sterile condition;
- a tubular keyway member extending coaxially about the cannula from the first connection site side of the plate, the tubular keyway member positioned coaxially about the cover; and
- a pair of pins extending between the second connection site side and the first connection site side.

13. A beneficial agent container and adapter assembly, comprising:
- a beneficial agent container having a chamber within which can be contained a beneficial agent and a closure having an injection site;
- an adapter configured to interconnect in fluid communication the beneficial agent container and a second connection site, the adapter including a plate having first and second connection site sides, a tubular wall including a radially outward extending lip which extends from the first connection site side and constructed such that the tubular wall allows containers having varying sized chambers to be secured thereto, a single removably covered cannula structure rigidly secured in the plate and flow path through the plate;
- a support secured to the beneficial agent container for removably receiving the adapter;
- a pair of detachable covers secured on opposite sides of the plate and about the cannula to maintain same in initial sterile condition, the support interconnecting the cover secured to the second connection site side of the plate and the beneficial agent container;
- a tubular keyway member positioned coaxially about the cover secured about the cannula on the first connection site side; and
- a pair of pins extending between the second connection site side and the first connection site side.

14. A beneficial agent delivery system comprising:
- a receptacle configured to deliver fluid to a patient, including a first connection site by means of which a beneficial agent can be introduced into the delivery system;
- an adapter for interconnecting in fluid communication the first connection site of the delivery system and a beneficial agent container having a closure with a second connection site and a chamber for containing a beneficial agent, the adapter including a plate having first and second connection site sides, a wall including a radially outward extending lip which extends from the plate from the second connection site side and configured to engage about only the closure of the beneficial agent container, and a single removably covered cannula structure rigidly secured in the plate and having a cannula extending through the plate;
- a beneficial agent container having the closure with the second connection site and a chamber within which can be contained a beneficial agent.
- a tubular single keyway member extending coaxially about the cannula from the first connection site side of the plate.
- a pair of pins extending between the second connection site side and the first connection site side and a cover secured about an end of the cannula extending from the second connection site side and being in interference fit with the pins; and
- means for removably coupling the adapter to the beneficial agent container prior to inserting the cannula through the closure.

* * * * *

UNITED STATES PATENT AND TRADEMARK OFFICE
CERTIFICATE OF CORRECTION

PATENT NO. : 5,423,753
DATED : Jun. 13, 1995
INVENTOR(S) : Thomas A. Fowles et al.

It is certified that error appears in the above-indentified patent and that said Letters Patent is hereby corrected as shown below:

Column 8, line 18: "a pair of pin" should be "a pair of pins".

Signed and Sealed this

Fifth Day of December, 1995

Attest:

BRUCE LEHMAN

Attesting Officer

Commissioner of Patents and Trademarks